United States Patent [19]

Lindner et al.

[11] Patent Number: 4,692,403
[45] Date of Patent: Sep. 8, 1987

[54] METHODS AND COMPOSITIONS FOR THE DETECTION OF ACQUIRED IMMUNE DEFICIENCY SYNDROME

[75] Inventors: Luther E. Lindner, College Station; Stephen R. Wechter, Houston, both of Tex.

[73] Assignee: The Texas A&M University System, College Station, Tex.

[21] Appl. No.: 675,601

[22] Filed: Nov. 28, 1984

[51] Int. Cl.$^4$ .................. C12Q 1/70; G01N 33/53; G01N 33/566; G01N 33/554

[52] U.S. Cl. ........................... 435/5; 435/7; 436/501; 436/519; 436/547; 436/804; 436/811; 436/813; 424/86; 530/387

[58] Field of Search .............. 436/501, 519, 800, 547, 436/813, 811, 63, 804; 435/5, 7; 424/86; 530/387

[56] References Cited

U.S. PATENT DOCUMENTS 4,298,685 11/1981 Parikh et al. .................. 435/188 X
4,520,113 5/1985 Gallo et al. .................... 436/531 X

OTHER PUBLICATIONS

Gallo et al (May 1984), Science 224:500–503.
Gallo et al (1983), Science 220:865–867.
Guange Guo, H. et al (1984–Mar.), Science 223:1195–1197.
Homma et al (Aug. 1984), Science 225:716–718.
Letvin et al (1983), Blood 61:408–410.
Haynes et al (1982), Science 215:298–300.
Kurth et al (1978), PNAS 75:5692–5696.
Markenson et al (Feb. 1984), Jour. of Immunol. 132:772–779.
Letvin et al, Proc. Natl. Acad. Sci. U.S.A., "Acquired Immunodeficiency Syndrome in a Colony of Macaque Monkeys", vol. 80, p. 2718 (May 1983).
Hunt et al, Proc. Natl. Acad. Sci. U.S.A., "Transmission of Naturally Occurring Lymphoma in Macaque Monkeys", vol. 80, p. 5085 (Aug. 1983).
London et al, *The Lancet*, "Experimental Transmission of Simian Acquired Immunodeficiency Syndrome (SAIDS) and Kaposi-like Skin Lesions", p. 869 (Oct. 15, 1983).
Marx et al, *Science*, "Simian AIDS: Isolation of a Type D Retrovirus and Transmission of the Disease", vol. 223, p. 1083 (Mar. 9, 1984).
Essex et al, *Science*, "Antibodies to Cell Membrane Antigens Associated with Human T-Cell Leukemia Virus in Patients with AIDS", vol. 220, p. 859 (May 1983).
Gelmann et al, *Science*, "Proviral DNA of a Petrovirus, Human T-Cell Leukemia Virus in Two Patients with AIDS", vol. 220, p. 862 (May 1983).
Eyster et al, *New Eng. J. Med.*, "Acid-Labile Alpha Interferon", vol. 309, p. 583 (Sep. 8, 1983).
Evatt et al, *The Lancet*, "Antibodies to Human T Cell Leukemia Virus-Associated Membrane Antigens in Haemophiliacs: Evidence for Infection Before 1980", p. 698 (Sep. 24, 1983).

(List continued on next page.)

*Primary Examiner*—Sidney Marantz
*Assistant Examiner*—Jack Spiegel
*Attorney, Agent, or Firm*—Arnold, White & Durkee

[57] ABSTRACT

An immunoreagent useful to diagnose Acquired Immune Deficiency Syndrome (AIDS) is provided. The immunoreagent comprises tracer tagged antibodies which are selectively reactive with lymphoid cells of AIDS infected tissue. The antibodies are obtained from marmoset monkeys which are either afflicted with or have recovered from Marmoset wasting syndrome. The immunoreagent is employed in a method to diagnose AIDS in a suspected carrier. The method involves admixing the immunoreagent such as marmoset serum or purified immunoglobulins together with lymphoid tissue samples taken from the suspected carrier. After incubating the admixture under appropriate conditions favorable for the formation of an immune complex, the samples are assayed for a positive immune reaction.

12 Claims, 4 Drawing Figures

OTHER PUBLICATIONS

Francioli et al, *Eur. J. Clin. Microbiol.*, "Beta-2 Microglobulin: A Sensitive Non-Specific Marker of Acquired Immune Deficiency Syndrome", vol. 3, p. 68.

Fuchs et al, *Eur. J. Clin. Microbiol.*, "Urinary Neopterin in the Diagnosis of Acquired Immune Deficiency Syndrome", vol. 3, p. 70.

Born et al, *Eur. J. Clin. Microbiol.*, "Presence of Viral Antibodies to the Human Lymphoma-Leukemia Virus in Patients with Acquired Immune Deficiency Syndrome", vol. 3, p. 77.

Prebble et al, *New Eng. J. Med.*, vol. 310, p. 923 (Apr. 15, 1984, Note.

Marwick, Co., *JAMA*, "French, US Viral Isolates Compared in Search for Cause of AIDS", vol. 251, p. 2901 (Jun. 8, 1984).

Zolla-Pazner et al, *JAMA*, "Quantitation of B2-Microglobulin and Other Immune Characteristics in a Prospective Study of Men at Risk for Acquired Immune Deficiency Syndrome", vol. 251, p. 2951 (Jun. 8, 1984).

Public Health Service, Centers for Disease Control, *Morbidity and Mortality Weekly Report*, vol. 33, p. 377 (Jul. 13, 1984) Note.

Klatzmann et al, *Science*, "Selective Tropism of Lymphadenopathy Associated Virus (LAV) for Helper-Inducer T Lymphocytes", vol. 225, p. 59 (Jul. 6, 1984).

Feorino et al, *Science*, "Lymphadenopathy Associated Virus Infection of a Blood Donor-Recipient Pair with Acquired Immunodeficiency Syndrome", vol. 225, p. 69 (Jul. 6, 1984).

Montagnier et al, *Science*, "Adaptation of Lymphadenopathy Associated Virus (LAV) to Replication in EBU-Transformed B Lymphoblastoid Cell Lines", vol. 225, p. 63 (Jul. 6, 1984).

Kalyanaraman et al, *Science*, "Antibodies to the Core Protein of Lymphadenopathy Associated Virus (LAV) in Patients with AIDS", vol. 225, p. 321 (Jul. 20, 1984).

METHODS AND COMPOSITIONS FOR THE DETECTION OF ACQUIRED IMMUNE DEFICIENCY SYNDROME

BACKGROUND OF THE INVENTION

The present invention relates to methods and compositions useful for the detection of Acquired Immune Deficiency Syndrome (AIDS). More particularly, this invention relates to antibodies which react positively with human AIDS tissues.

Acquired Immune Deficiency Syndrome (AIDS), also known as Gay-Related Immune Deficiency or Gay Compromise Syndrome is apparently a new disease of man which prior to 1981 was not recognized as a specific disease entity. To date, with over 4,000 cases reported, the disease has elicited great concern because the epidemic is quickly expanding and the disease exhibits a very high mortality rate.

At present, the disease is defined by its clinical features, as no specific diagnostic test has been reported. Young infants (less than 28 days) and the elderly (over 60 years) are excluded by definition, as other causes of deficient cellular immunity can affect these age groups. Also by definition, all other known causes of immune deficiency such as a neoplasm (except those specifically associated with AIDS), immunosuppressive therapy, corticosteroid therapy and renal failure are excluded. To be diagnosed as having AIDS, a patient must have a disease that specifically indicates a deficiency in cellular immunity such as Kaposi's sarcoma, primary central nervous system lymphoma, progressive multi-focal leukoencephalopathy, or infections with a variety of organisms that are not usually seen as pathogens, including *Pneumocystis carinii*, *Toxoplasma gondii*, cryptosporidium, cytomegalovirus, disseminated fungal infections particularly with Aspergillus, Cryptococcus, Candida, Nocardia, disseminated herpes viruses, atypical Mycobacteria, or uncontrolled *Strongyloides stercoralis* infestation. Typically more than one of these is seen in the patient and there are concomitant abnormalities of immune function which can be demonstrated by laboratory tests but which are not specific to AIDS. Kaposi's sarcoma and *Pneumocystis carinii* pneumonia have been the most characteristic diseases. Once the characteristic clinical picture of AIDS is established in a patient, immune function does not revert to normal.

Prior to the development of AIDS, patients have a prodromal illness characterized by fever, weight loss and enlarged lymph nodes. This may last for weeks to years. This lymphadenopathy syndrome is not specific to AIDS, similar cases having been described long before AIDS appeared; and only a minority of patients with this clinical syndrome, even in high-risk groups, have gone on to develop AIDS.

The epidemiology of AIDS strongly suggests involvement of an infectious agent such as a virus. AIDS has been largely confined to homosexual and bisexual sexually promiscuous males, Haitians, intravenous drug abusers, hemophiliacs, and other recipients of blood and blood products. The disease has a very long incubation period, making the chains of transmission difficult to follow. The disease is transmitted with some difficulty and requiring either intimate contact, particularly anal intercourse, or actual transfer by blood.

A variety of agents have been suggested as possible causes. Viruses are regularly recovered from patients with the disease, including cytomegalovirus, Epstein-Barr virus, and adenoviruses. The most likely etiologic agents include retroviruses which have been cultured from a significant percentage of patients by investigators at the National Cancer Institute (NCI) and at the Institute Pasteur. The agent cultured at the NCI is characterized as a variant of the human T-cell leukemia virus, names HTLV-III. It has been cultured from a high percentage of patients with the prodromal syndrome. Although antibodies to it are seen in a high percentage of patients with AIDS, it has only been cultured from about one third of patients who actually have AIDS. Comparable data is presently available concerning the viruses cultured by the French workers. At this time, no proof exists that either of these viruses is in fact the cause of AIDS, although both groups claim that their virus is the cause.

Presently, there are no laboratory tests available which are specific for AIDS. A number of different abnormalities of immune function can be demonstrated, such as failure to respond to skin testing for common cellularimmunity-based recall antigens, altered blood lymphocyte levels, and altered ratios of helper and suppressor subsets of T-lymphocytes. These abnormalities are merely expressions of the immune defect and can be produced by many different causes. Abnormal levels of alpha-thymosin, alpha-interferon, neopterin and $beta_2$-microglobulin, have also been noticed. Again, these are nonspecific indicators and may reflect an immune defect or the presence of an inflammatory stimulus rather than any specific disease.

A specific test for AIDS requires an antibody or immunoprotein specific for the etiologic agent or something the etiologic agent produces in the involved tissues. The only candidate for such an antibody has been derived from patients with AIDS or the pre-AIDS syndrome. These antibodies which can be used to identify viral components in AIDS tissue require a difficult and tedious assay procedure. Although antibodies directed against HLTV-III are presently being developed, they may still require difficult assay procedure to elicit detection of AIDS. Moreover, there is no conclusive proof that HTLV-III is the cause of AIDS.

Several animal models have been suggested as closely related to AIDS, including AIDS-like diseases in rhesus monkeys and macaques. Viruses have been cultured from these animals, but these viruses do not appear to be related to HTLV-III. These animals do not survive the disease and have not been reported as a source of antibodies. Attempts have also been made to transfer the human disease to rhesus monkeys and chimpanzees, but neither viruses nor antibodies have been reported from these animals. At present there is no recognized animal model for AIDS.

Accordingly, there is a great need for a diagnostic test or procedure capable of detecting AIDS in a suspected carrier.

SUMMARY OF THE INVENTION

The present invention provides an immunoreagent comprising antibodies capable of reacting selectively with lymphoid cell samples obtained from AIDS-infected individuals. More particularly, the immunoreagent is serum, or immunoglobulin isolated from the serum, of marmoset monkeys afflicted with or recovering from, marmoset wasting disease. In another aspect of the invention the immunoreagent comprises tracer tagged antibodies.

Moreover, the present invention provides a method for immunodiagnosing AIDS in a person infected with or suspected of carrying the disease. The method involves incubating a lymphoid cell sample, such as lymphatic tissue or blood, from the suspected carrier together with the tracer tagged antibody-containing immunoreagent obtained from marmoset monkeys afflicted with or recovered from marmoset wasting disease. A positive immunoreaction indicating that the person has AIDS is exhibited by a staining of the membranes of cytoplasmic vacuoles or other cytoplasmic membrane-associated structures of lymphocytes.

DETAILED DESCRIPTION OF THE INVENTION

Figure 1:
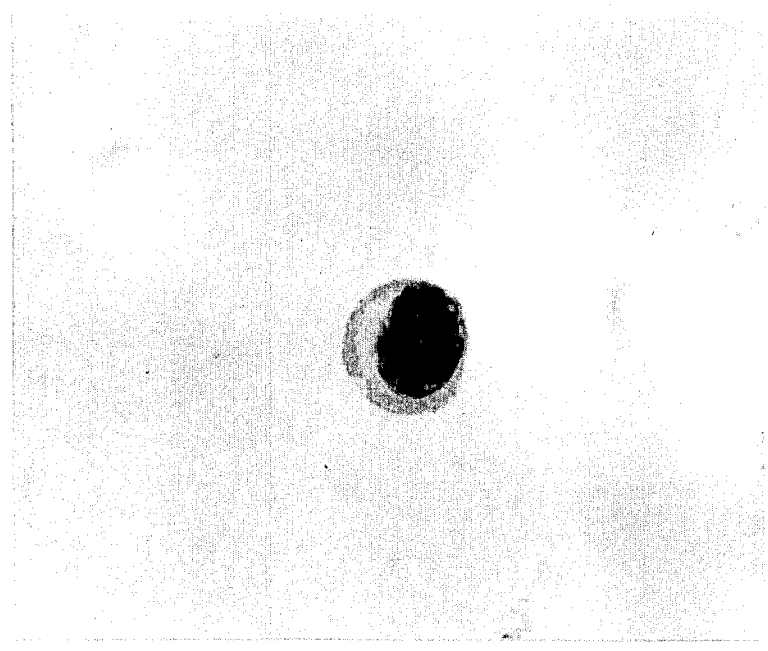
FIG. 1 is a positive lymphocyte staining indicative of AIDS.

Immunological diagnosis of a pathogenic disease state normally requires an antibody that is specific for an antigen which is produced in connection with the disease state. In viral disease, antigens produced by the viral infection can be detected by an immunoreaction with an antibody selective for the viral antigens. However, selective generation of such antibody generally requires knowledge of the viral agent. One generally must have isolated, or at least identified, the causative viral agent before a specific antibody can be developed. However, in the case of AIDS, no viral agent has been specifically identified as the causative agent.

The present invention takes advantage of the fact that marmoset monkeys produce immunoglobulin containing an antibody, or series of antibodies, capable of reacting selectively with lymphoid cells obtained from patients infected with the AIDS causative agent. Applicants have observed that marmosets which are either afflicted with or recovering from a disease state, referred to as marmoset wasting syndrome, are capable of producing an AIDS-selective antibody. This marmoset wasting syndrome antibody reacts selectively with lymphocytes from AIDS-infected individuals.

MARMOSET MODEL FOR AIDS

At Texas A&M University in the College of Veterinary Medicine there is a colony of common marmosets (*Callithrix jacchus*) which has been maintained as a research resource. Several years ago some of these animals were noted as having a chronic wasting disease. Although for some time this was believed to be a problem that made the sick animals unsuitable for research, a distinct disease syndrome was recognized, characterized by weight loss, loss of hair, and opportunistic infections. Although the pattern of disease is not identical to human AIDS, in particular these animals do not have an identical spectrum of infections nor do they have neoplasms such as Kaposi's sarcoma, the differences are thought to be related to species differences.

A relationship between the marmoset wasting syndrome and human AIDS is evident. These afflicted animals have a decreased ratio of helper to suppressor T-lymphocyte subsets, decreased lymphocyte activation in blastogenesis assays, and similar disturbances of antibody production as seen in human AIDS.

While the marmoset wasting syndrome is similar to AIDS, a crucial difference exists, namely a significant population of infected marmosets recover from the disease.

PREPARATION OF THE AIDS-SELECTIVE ANTIBODY

Three marmosets were identified in the study population that were documented as having recovered from the wasting syndrome. Blood was drawn from these animals by femoral puncture, allowed to clot, and the serum was separated and pooled. An equal volume of 0.05 M phosphate-buffered normal saline (PBS), pH 7.2 was added to the serum. In a cold room (temperature approximately 4° C.), saturated ammonium sulfate, pH 7.6, was added dropwise with stirring to 50% saturation. The resulting globulin mixture was allowed to stir for 30 minutes and then centrifuged in a swinging bucket rotor at 1000 RCF at 4° C. The supernatant fraction was decanted and discarded and the precipitate was dissolved in PBS. Saturated ammonium sulfate was again added dropwise to 50% saturation and the globulin mixture stirred and centrifuged as before. The precipitated globulin was redissolved in PBS and dialysed overnight against PBS. Next, the globulin fraction was centrifuged at 1000 RCF for 10 minutes at room temperature. The supernatant globulin fraction in 0.25 ml aliquots was stored by freezing at −70° C..

The globulin fraction was further purified to immunoglobulins by adsorption through a protein A-agarose column. The globulin fraction was thawed and adsorbed onto the column for an hour. The column was then washed with multiple volumes of PBS for at least an hour. Immunoglobulin containing antibody was eluted with 0.5% acetic acid in 0.15M NaCl and the fractions collected. The protein peak as identified at $OD_{280}$ was pooled. The pooled immunoglobulin protein fractions were dialysed overnight against two changes of PBS.

For subsequent reaction, the immunoglobulin fraction was biotinylated by dialysis against 0.1M $NaCO_3$-$NaHCO_3$, pH 9.0 for 4 hours. Then 0.12 ml of a 1% solution of N-hydroxy-succidiminobiotin was added to 1 ml of immunoglobulin fraction and incubated at room temperature for 3–3½ hours. The product was dialysed against PBS overnight. Since initial batchs of immunoglobulin were unstable and had excessive nonspecific reaction, subsequent lots were stabilized by addition of a small amount (unmeasured) of alpha-1 antitrypsin and adsorbed against acetone-dried tonsil or spleen for several hours.

The adsorption was made by adding small fragments of the tissue to the immunoglobulin preparation and incubating them together at 4° C. for three to six hours. Then the gross tissue was removed and the immunoglobulin filtered through 0.2 micron pore membrane filter.

IMMUNOHISTOCHEMICAL STAINING OF TISSUE SAMPLES

This immunoglobulin fraction containing antibody reactive against AIDS tissue was used for immunohistochemical staining using the following procedure. Formalin-fixed paraffin embedded tissue sections were deparaffinized in xylene and rehydrated through graded ethanol to $H_2O$. Alternatively, air-dried blood films were fixed in formalin and washed in H₂O. Endogenous peroxidase activity was blocked with 3% $H_2O_2$-MeOH 1:4 for 5 minutes. The slides were rinsed in PBS and incubated with the biotinylated immunoglobulin fraction diluted in 1:200 in PBS for 30 minutes to 1 hour. Control slides were incubated with PBS. Slides were washed in PBS and incubated in Avidin DH-biotin-peroxidase complex for 45 minutes (Vectastain, Vector Laboratories, Burlingame, CA). All subsequent steps following the Vectastain procedure used diaminobenzidine as the chromogen at a concentration of 0.02%. Slides were counterstained with 0.05% toluidine blue in 80% ethanol for 10 seconds, washed, dehydrated, and mounted.

The biotinylated immunoglobulin fraction reacted specifically with lymphocytes in lymphatic tissue and serum from wasted marmosets and human AIDS patients.

The actual tissue component (antigen) that the antibody is reacting with is unknown, but it appears to be associated with cytoplasmic membrane structures of some sort. Applicants first destroy any peroxidase activity that might naturally be present in the tissue. The tissue or blood is then incubated with antibody. The active site of which binds to the antigen with a high affinity (typical of antibodies) so that the antibody is not removed from the antigen in the washes, although it is washed out of all other sites. This antibody has been previously coupled to a tracer such as in this instance biotin. The biotin moieties on the antibody are free to react with free sites on avidin, a protein from egg white that binds to biotin with high affinity. The avidin is also previously coupled to biotinylated peroxidase molecules so that it becomes a bridging molecule. The peroxidase then becomes an indicator of the presence of the antigen via a multistep bridge. The peroxidase is visualized by reacting it with hydrogen peroxide and one of a large number of possible compounds that give a colored oxidation product. Applicants have been using diaminobenzidine because it gives better localization than most of the alternatives, but it has no other special virtue. The oxidized diaminobenzidine is a colored precipitate that is easily visualized in the microscope.

EXAMPLE I

Immunohistochemical Staining of Human AIDS Tissue

Sections were stained of a variety of tissues from 8 AIDS autopsies and 12 non-AIDS autopsies as well as lymph node and/or spleen from 5 normal or hyperplastic non-AIDS patients and a plasmacytoma from a non-AIDS patient.

In the AIDS patients there was specific staining of lymphocytes and macrophages from all cases either of multiple membrane profiles in the cytoplasm or of localized, particularly ring-shaped profiles representing vacuolar membranes. One frequent pattern of staining was of ring-shaped profiles and more diffuse structures in the general region of the Golgi region of the cell. No nuclear staining was seen but nuclear membranes sometimes stained.

The non-AIDS lymphoid tissue either didn't stain or showed nonspecific staining, with the single exception of the plasmacytoma, which stained specifically. The intensity of staining and the presence of nonspecific staining appeared to be affected by tissue fixation, with poorly fixed tissues (as recognized by the usual morphologic criteria) staining nonspecifically or weakly.

EXAMPLE II

Screening of Blood Specimens

Twenty-three blood smears from normal, non-AIDS and AIDS patients were stained with the immunoglobulin immunoreagent. These human smears showed changed that could allow successful blind classification into AIDS or non-AIDS.

The 10 AIDS cases showed relatively diffuse or somewhat granular staining of the cytoplasm, particularly of large atypical lymphocytes, but also to some degree macrophages. FIG. 1 is representative of lymphocyte staining in AIDS patients. Artifactual nonspecific staining of eosinophils was also seen but easily distinguished.

Figure 2:
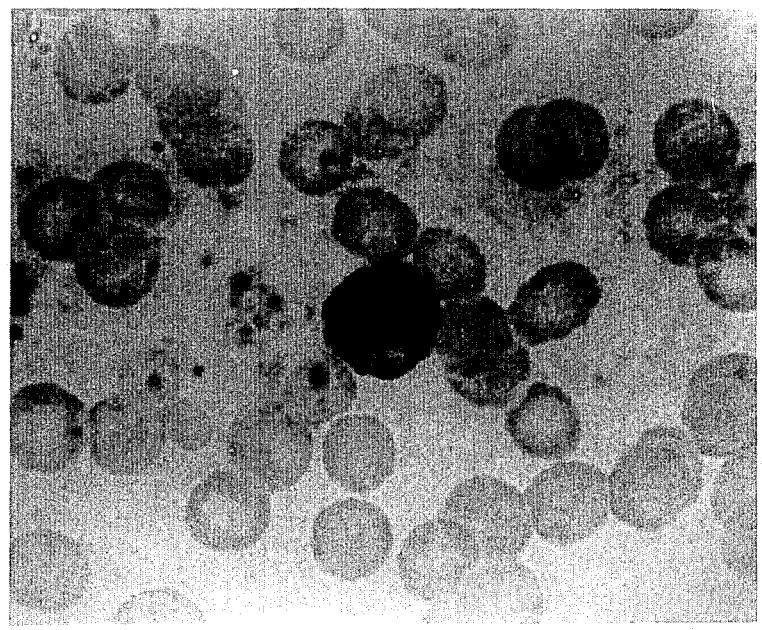
FIG. 2 is a positive lymphocyte staining indicative of AIDS, in particular the patient from whom this sample was taken was in the prodrome of AIDS.

In 10 patients in the prodromal stages a weakly positive staining was observed as represented by FIG. 2.

In 3 of 4 smears of non-AIDS illnesses no staining was seen. One case of infectious mononucleosis stained, but with a cell pattern subtly different from the AIDS cases.

Figure 3:
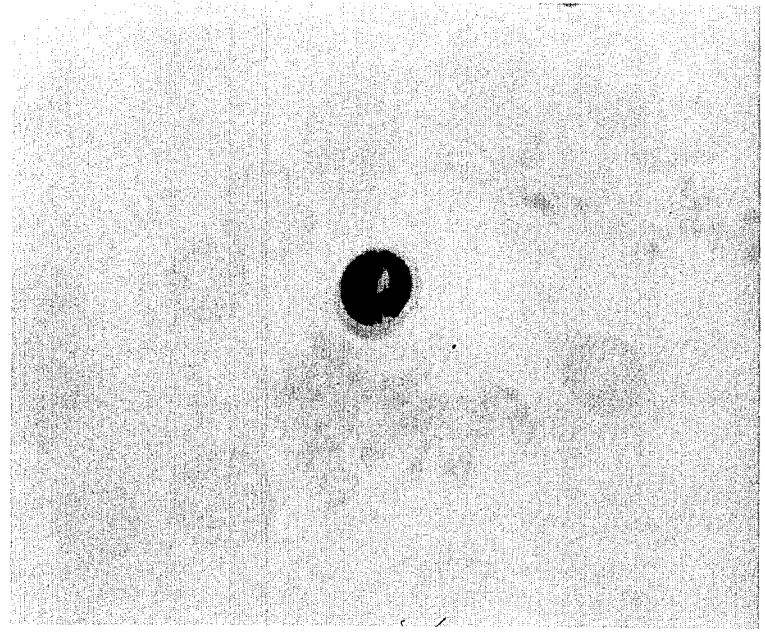
FIG. 3 shows negative staining of a blood smear sample taken from a normal healthy homosexual.
Figure 4:
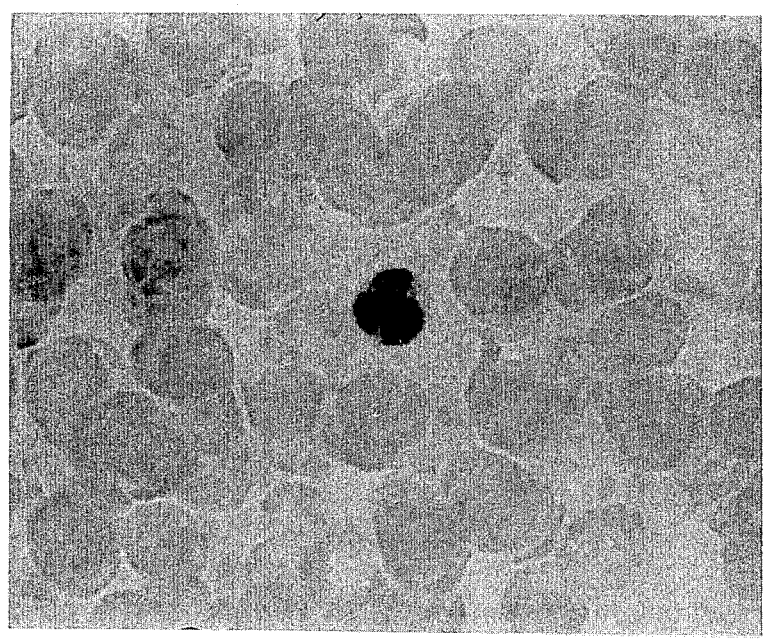
FIG. 4 shows a negative control sample.

FIGS. 3 and 4 show staining of normal lymphocytes.

CRITERIA TO DISTINGUISH POSITIVE VERSUS NEGATIVE OR NONSPECIFIC STAINING

The criteria that have been applied to recognize a positive reaction versus nonspecific staining versus a negative reaction include:

1. The cells being stained must be lymphoid. Staining of other cell types has not been shown to be specific.

2. The staining must be of discrete individual cells out of the population. Uniform staining of all cells is not specific.

3. In poorly fixed tissue, there is a tendency for staining of the plasma membrane, the nuclear membrane, or diffusely through the cells. This involves most of the cells in the specimen. This is an artifact and should not be interpreted as positive. Staining of the nucleus may also be nonspecific.

4. There will always be a weak generalized staining of the tissue due to nonspecific binding of antibody to various components of the tissues, especially highly charged groups. This must not be interpreted as positive.

5. In tissue sections, positive staining is seen as localized staining of portions of the cytoplasm of individual cells, typically plasmacytoid cells which are large irregular lymphoid cells. Two patterns of staining have been recognized. One pattern is staining of the membranes of vesicles and/or more diffuse staining which occurs in the general vicinity of the Golgi apparatus, i.e., an area near the nucleus at the pole where the most cytoplasm is concentrated. The other pattern is staining of discrete membranes of very small round vesicles which can occur anywhere in the cytoplasm and which may be associated with staining of other more irregular membranes in the cytoplasm and/or the nuclear membrane. These vesicles are seen clearly only at large magnifications, but they tend to stain very intensely. Staining of the plasma membrane is also sometimes seen but it not acceptable as a criterion for positive staining. It is not clear whether one of these patterns is more sensitive or more specific than the other from present data, although the Golgi region staining is suspected to be more sensitive, but the staining of discrete vesicles and membranes is more specific.

For blood smears, the criteria are slightly different. The staining appears to be less discrete although again only cytoplasmic staining is considered. Positive smears show staining of individual lymphocytes, especially large lymphocytes. Other cell types are not considered. Positive staining is seen in the cytoplasm especially adjacent to the plasma membrane and involving the plasma membrane, and appears to be somewhat clumpy or granular. Diffuse staining of the cytoplasm is not interpreted as positive.

6. The color of the reaction product varies from brown to gray depending on the amount of counterstain present in the same area. The blue of the counterstain should not be interpreted as reaction product. Good color vision is required for interpretation particularly as the gray color that is often produced is subtle to see. Microscope optics affect the perception of the colors in the slides and therefore the use of good, quality, carefully selected optics is important.

The foregoing description has been directed to particular embodiments of the invention for the purposes of illustration and explanation. Those skilled in the art will readily appreciate modifications and changes in the procedures and compositions set forth without departing from the scope and spirit of the invention.

In particular, Applicants contemplate that a monoclonal antibody composition developed from a marmoset antibody selectively reactive to an AIDS antigen or AIDS infected lymphocyte would provide yet another particularly preferred immunoreagent useful to carry out the immonodiagnosing methods of this invention.

Indeed, the marmoset anti-AIDS antibodies can be used in one or more of other many ways as a diagnostic test. In particular, the antibodies can be tagged by conventional techniques with tracers such as radioisotopes, fluorescent labels, or fluorogenic enzymes. Such tagged antibodies are extremely useful in diagnostic tests. Various approaches can be utilized including both direct and indirect immunoassays. Variations on the general immunoassay theme include radioimmunoassay (direct or indirect), fluorescent antibody techniques (direct or indirect) enzyme-linked immunosorbent assays (ELISA's), inhibition of hemolysis assays, inhibition of agglutination tests, agglutination reactions (antibody-ligand mediated), and/or complement consumption tests. The use of one or more anti-AIDS antibodies in such systems constitute an important new and useful test for the diagnosis of AIDS and can be employed in very sensitive type immunoassays.

Applicants' intent is that the following claims be interpreted to embrace all such modifications and variations.

What is claimed is:

1. A method of immunodiagnosing Acquired Immune Deficiency Syndrome in a suspected carrier comprising:
   (a) admixing a lymphoid cell sample obtained from the suspected carrier with an immunoreagent comprising tracer tagged antibodies selectively reactive with AIDS infected tissue, said antibodies obtained from marmoset monkeys, wherein the marmoset monkeys are either afflicted with or have recovered from marmoset wasting syndrome;
   (b) incubating the admixture under conditions to form an immune complex; and
   (c) detecting a positive immunoreaction which is indicative of Acquired Immune Deficiency Syndrome.

2. The method of claim 1 wherein the suspected carrier is a human.

3. The method of claim 1 wherein the lymphoid cell sample is blood.

4. The method of claim 1 wherein the lymphoid cell sample is lymphatic tissue.

5. The method of claim 1 wherein the lymphoid cell sample is splenic tissue.

6. The method of claim 1 wherein the immunoreagent is serum.

7. The method of claim 1 wherein the immunoreagent consists essentially of immunoglobulins.

8. The method of claim 1 wherein the tracer tagged antibodies are covalently linked to biotin.

9. The method of claim 1 wherein the tracer tagged antibodies comprise antibody covalently linked to a radioisotope, a fluorogenic enzyme, or a fluorescent label.

10. An immunoreagent useful to diagnose Acquired Immune Deficiency Syndrome, comprising tracer tagged antibodies selectively reactive with AIDS infected tissue, said antibodies obtained from marmoset monkeys, wherein the marmoset monkeys are either afflicted with or have recovered from marmoset wasting syndrome.

11. The immunoreagent of claim 10 wherein the tracer tagged antibodies comprise antibody covalently linked to biotin.

12. The immunoreagent of claim 10 wherein the tracer tagged antibodies comprise antibody covalently linked to a radioisotope, a fluorogenic enzyme, or a fluorescent moiety.

* * * * *